(12) United States Patent
Eviston et al.

(10) Patent No.: US 11,324,758 B2
(45) Date of Patent: May 10, 2022

(54) FORMULATION AND PROCESS FOR LIMITING NERVE TRAUMA

(71) Applicant: Intravital Pty Ltd, Randwick (AU)

(72) Inventors: Timothy J. Eviston, Randwick (AU); Arun Krishnan, Randwick (AU)

(73) Assignee: Intravital Pty Ltd, Randwick (AU)

( * ) Notice: Subject to any disclaimer, the term of this patent is extended or adjusted under 35 U.S.C. 154(b) by 0 days.

(21) Appl. No.: 15/579,224

(22) PCT Filed: Jun. 2, 2016

(86) PCT No.: PCT/AU2016/050445
§ 371 (c)(1),
(2) Date: Dec. 4, 2017

(87) PCT Pub. No.: WO2016/191820
PCT Pub. Date: Dec. 8, 2016

(65) Prior Publication Data
US 2018/0185390 A1  Jul. 5, 2018

(30) Foreign Application Priority Data

Jun. 2, 2015 (AU) .............................. 2015902089
Jul. 7, 2015 (AU) .............................. 2015902669
Aug. 3, 2015 (AU) .............................. 2015903087

(51) Int. Cl.
*A61K 9/24* (2006.01)
*A61K 31/573* (2006.01)
(Continued)

(52) U.S. Cl.
CPC ............ *A61K 31/573* (2013.01); *A61B 5/389* (2021.01); *A61F 9/0008* (2013.01);
(Continued)

(58) Field of Classification Search
CPC ... A61B 5/0488; A61K 31/573; A61K 9/0024
See application file for complete search history.

(56) References Cited

U.S. PATENT DOCUMENTS 6,238,702 B1    5/2001  Berde et al.
8,190,271 B2    5/2012  Overstreet et al.
2009/0263456 A1  10/2009  McKay

FOREIGN PATENT DOCUMENTS

WO    2002043785    6/2002
WO    2008157057    12/2008
(Continued)

OTHER PUBLICATIONS

International Search Report for Application No. PCT/AU2016/050445 dated Jul. 26, 2016 (8 pages).
(Continued)

*Primary Examiner* — Benjamin J Packard
(74) *Attorney, Agent, or Firm* — Michael Best & Friedrich LLP

(57) ABSTRACT

Disclosed in some forms is a process of limiting the impact of surgery on a nerve, the process comprising applying a therapeutic substance to the nerve during surgery. In some aspects, disclosed is a formulation for reducing nerve trauma comprising an active pharmacological ingredient adapted to intervene in the activation of pathways of cellular degradation within the nerve and a carrier adapted to reduce dissemination of the active pharmacological ingredient beyond the site at which its effect is intended.

8 Claims, 4 Drawing Sheets

(51) Int. Cl.

| | |
|---|---|
| *A61M 5/48* | (2006.01) |
| *A61F 9/00* | (2006.01) |
| *A61K 9/00* | (2006.01) |
| *A61M 5/315* | (2006.01) |
| *A61M 5/142* | (2006.01) |
| *A61M 5/24* | (2006.01) |
| *A61B 5/389* | (2021.01) |
| *A61K 47/36* | (2006.01) |
| *A61B 17/34* | (2006.01) |
| *A61M 5/31* | (2006.01) |
| *A61M 39/18* | (2006.01) |
| *A61M 5/00* | (2006.01) |
| *A61B 90/00* | (2016.01) |

(52) U.S. Cl.
CPC ............ *A61K 9/0024* (2013.01); *A61K 47/36* (2013.01); *A61M 5/14248* (2013.01); *A61M 5/24* (2013.01); *A61M 5/2422* (2013.01); *A61M 5/31565* (2013.01); *A61M 5/31595* (2013.01); *A61M 5/48* (2013.01); *A61B 17/3472* (2013.01); *A61B 2090/3933* (2016.02); *A61B 2090/3941* (2016.02); *A61B 2505/05* (2013.01); *A61M 5/2466* (2013.01); *A61M 5/315* (2013.01); *A61M 39/18* (2013.01); *A61M 2005/005* (2013.01); *A61M 2005/3117* (2013.01); *A61M 2205/0266* (2013.01); *A61M 2205/13* (2013.01); *A61M 2205/586* (2013.01); *A61M 2205/8206* (2013.01)

(56) References Cited

FOREIGN PATENT DOCUMENTS

| | | |
|---|---|---|
| WO | 2014116876 | 7/2014 |
| WO | 2016118649 A1 | 7/2016 |

OTHER PUBLICATIONS

International Preliminary Report on Patentability for Application No. PCT/AU2016/050445 dated Oct. 11, 2017 (36 pages).

Ito, T. et al., "Anti-inflammatory function of an in situ cross-linkable conjugate hydrogel of hyaluronic acid and dexamethasone," Biomaterials, 2007, vol. 28, Issue 10, pp. 1778-1786.

Ozsoy, Z. et al., "The effect of methylprednisolone and tenoxicam on the protection of damage of the nerve physiomorphology caused by prolene mesh," International Journal of Surgery, 2015, vol. 22, pp. 159-163.

European Patent Office Extended Search Report for Application No. 16802250.7 dated Jan. 28, 2019, 9 pages.

Ikeda et al., "Hyaluronic acid prevents peripheral nerve adhesion." Br J Plast Surg. 2003; 56(4):342-7.

FORMULATION AND PROCESS FOR LIMITING NERVE TRAUMA

BACKGROUND

The present invention relates to limiting trauma to a nerve, and to a formulation, delivery system and process for limiting trauma to a nerve. The formulation and process particularly limit the impact of surgery or other event or activity on a nerve, however the formulation and process are not limited to those applications. The delivery system is particularly suited to delivering a therapeutic substance during surgery but is not limited to that application

SUMMARY

Disclosed in some forms is a process of limiting the impact of surgery on a nerve, the process comprising applying a therapeutic substance to the nerve during surgery.

In some forms the therapeutic substance is selected from substances that can intervene in the activation of pathways of cellular degradation within the nerve.

In some forms the therapeutic substance comprises an active pharmacological ingredient and a carrier.

The process has the benefit of limiting nerve trauma for patients during surgery or dental surgery by providing a predictable localisation and consistent rate-limited delivery of an active pharmaceutical ingredient that reduces the trauma on nerves through surgery. The delivery of the active pharmaceutical ingredient directly to the nerve during surgery improves nerve function and repair post surgery.

In some aspects, disclosed is a formulation for reducing nerve trauma comprising an active pharmacological ingredient adapted to intervene in the activation of pathways of cellular degradation within the nerve and a carrier adapted to reduce dissemination of the active pharmacological ingredient beyond the site at which its effect is intended.

The formulation includes an active pharmaceutical ingredient and a carrier that provides benefits such as slow release and localisation of the active pharmaceutical. The active pharmaceutical ingredient therefore is more likely to remain on the intended site of effect.

In other aspects, disclosed is use of a formulation as described during surgery.

In some forms the use comprises applying the formulation to a nerve that has been exposed during surgery.

Disclosed in some forms is a method of delivering a therapeutic substance during surgery, the method comprising loading a solid phase or gel phase biodegradeable scaffold with a therapeutic substance; and positioning the scaffold during surgery such that the therapeutic substance is delivered to a desired location.

During surgery, internal delivery sites for therapeutic substances are exposed allowing for positioning of a scaffold to allow positioning of the material such that it remains in one place, and delivery of the substance over a period of time at a sustained rate.

In some forms the therapeutic substance is selected from substances that can intervene in the activation of pathways of cellular degradation within the nerve and the desired location is proximal to a nerve.

In some forms the method allows for delivery of a therapeutic substance and a haemostatic agent in combination.

In other aspects, disclosed is a system for delivering a therapeutic substance during surgery, the system comprising a solid phase biodegradable scaffold with a therapeutic substance loaded thereon.

The method and system may provide for improved levels of pain management, improved delivery of the therapeutic substance, improved recovery, improved muscle function, improved autonomy, or improved sensation. In some forms chronic pain or inflammation can be reduced or avoided. In some forms delivery of the drug beyond a selected site is minimised.

In some forms the method of delivery allows differentiation of delivery of different therapeutic substances.

In some forms, disclosed is a formulation comprising an active pharmacological ingredient having a neuroprotective effect and a carrier adapted to reduce dissemination of the active pharmacological ingredient beyond the site at which its effect is intended.

In some forms, disclosed is a process of protecting a nerve during surgery, the process comprising identifying a nerve using a nerve monitor and applying a therapeutic substance to the nerve. In some form the process further comprises the step of monitoring the nerve function by monitoring EMG activity from muscles innervated by the affected nerve.

The process, formulation and delivery system may provide for improved levels of pain, improved recovery, improved muscle function, improved autonomy, or improved sensation. In some forms chronic pain or inflammation can be reduced or avoided. They may provide for improved effectiveness of treatment.

BRIEF DESCRIPTION OF THE FIGURES

The disclosure will be described in view of the Figures.

DETAILED DESCRIPTION OF EMBODIMENTS OF THE DISCLOSURE

Figure 1:
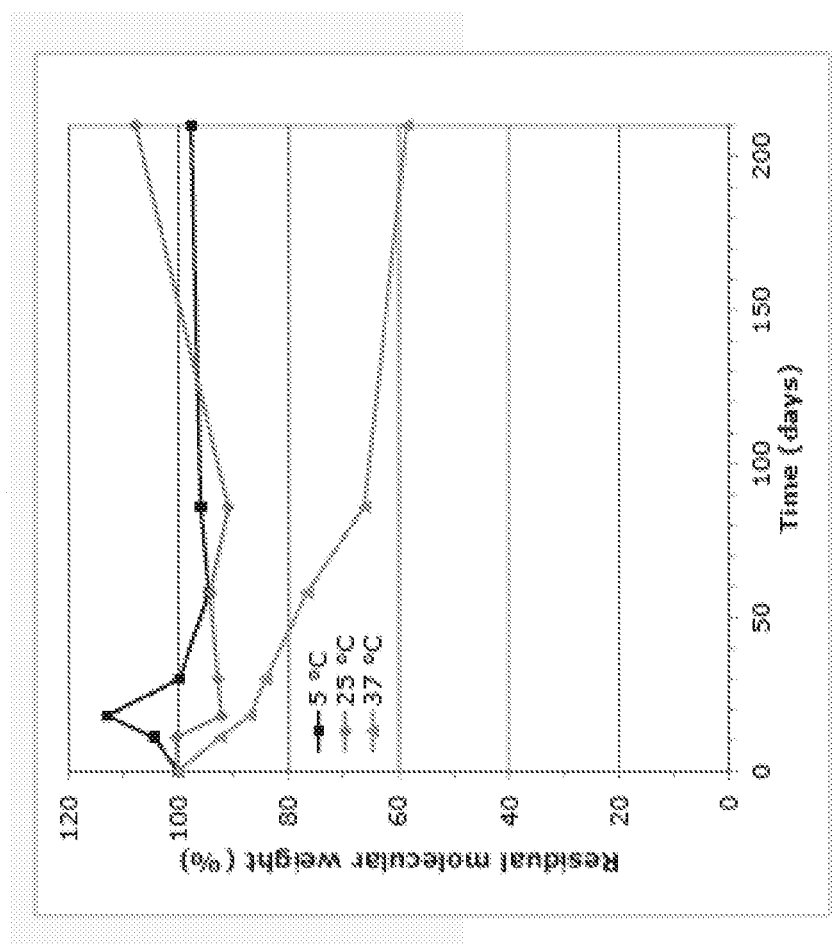
FIG. 1 is a graphical representation of molecular weight v time for hyaluronic acid with dexamethasone as in some embodiments of the disclosure.

Disclosed in some forms is a process of limiting the impact of surgery on a nerve, the process comprising applying a therapeutic substance to the nerve during surgery.

In some forms the therapeutic substance is selected from substances that can intervene in the activation of pathways of cellular degradation within the nerve. In some forms the formulation interrupts or downregulates intra-axonal pathways of cell death or degradation during the course of a surgical procedure. In some forms the therapeutic substance has a neuroprotective effect.

In some forms the therapeutic substance comprises an active pharmacological ingredient and a carrier.

In some forms the carrier is a depot matrix. In some forms the carrier is adapted to slow the release of the active pharmacological ingredient.

In some forms the carrier has a consistency and rheology adapted to reduce dissemination of the active pharmacological ingredient beyond the site at which its effect is intended.

In some forms the carrier is adapted to localise the active pharmacological ingredient to the site at which its effect is intended.

In some forms the active pharmacological ingredient is a corticosteroid. In some forms the pharmacological ingredient is dexamethasone.

In some forms the active pharmacological ingredient is hydrocortisone, methylprednisone, triamcinolone, Betamethasone or any other corticosteroid.

In some forms the active pharmacological ingredient is any of a number of medications which have a neuroprotective effect or act to decrease nerve dysfunction. This may include any one or more of 4-Aminopyridine (or derivatives eg. Fampridine), Riluzole, NAD altering molecules such as nicotinamide mononucleotide, CD38 and cyclic ADP ribose hydrolase inhibitors, nicotinamide riboside, AICAR, resveratrol, thiazolidinediones (eg. rosiglitazone, pioglitazone etc), metformin, local anaesthetics (eg. bupivicaine), cyclosporin, tacrolimus, COX inhibitors (eg. ketorolac, diclofenac), calcium channel blockers (eg. nifedipine), pipaverine, dexpramiprexole.

In some forms the active pharmacological acts by improving mitochondrial function or inhibiting calcium or cell death pathways.

Surgical nerve injury peripheral to the surgery is a danger of surgery. Nerve dysfunction can result from trauma to the nerves despite the nerves appearing to be intact. This makes nerve dysfunction difficult to predict during surgery. Traumatic mechanisms such as stretch, thermal injury, electrical injury, compression and ischaemia can accumulate to cause activation of pathways of cellular degradation within a nerve's axon. This can cause nerve break down and loss of function.

The process of controlled application of a formulation directly to a nerve that can intervene in pathways of cellular degradation has the impact of reducing the potential of trauma to the nerve or reducing the effects of that trauma. This trauma can occur even in circumstances where that trauma is not visible. Thus application of dexamethasone or an alternative active pharmaceutical ingredient to a nerve during surgery can limit or prevent peripheral nerve injury occurring during surgery.

In some forms the step of applying a therapeutic substance to the nerve is performed upon exposure of the nerve during surgery.

In some forms, the step of applying a therapeutic substance to the nerve is performed using a delivery device comprising a reservoir and an outlet, the therapeutic substance being delivered through the outlet.

In some forms actuation of the delivery device effects delivery of the formulation during the time at which the actuator is actuated.

Further, disclosed is a formulation for reducing nerve trauma comprising an active pharmacological ingredient adapted to intervene in the activation of pathways of cellular degradation within the nerve and a carrier adapted to slow release to prolong the pharmacokinetics of the active pharmaceutical, and to reduce dissemination of the active pharmaceutical ingredient beyond the site at which its effect is intended.

In some forms the active pharmacological ingredient is effective to limit nerve dysfunction or have a neuroprotective impact.

The active pharmaceutical ingredient may also include a prodrug, biologic, immunoglobulin, viral vector, gene therapy, immunotherapy, DNA plasmid, RNA inhibitor or protein or peptide.

The formulation allows the application of an active pharmaceutical ingredient to a nerve while limiting the application of that ingredient to surrounding cells. This may provide greater concentration of the active pharmaceutical to the relevant cells and limits waste. The formulation can also act to slow release of the active pharmaceutical ingredient.

The formulation, in some embodiments of the disclosure, comprises a corticosteroid such as dexamethasone in the form of dexamethasone phosphate or dexamethasone sodium phosphate in hyaluronic acid. In some forms the formulation comprises dexamethasone sodium phosphate, in a hydrogel of hyaluronic acid. In some forms the formulation further includes any one of more of the excipients creatinine, sodium citrate, sodium sulphate, methyl paraben, propylparaben. In some forms the hyaluronic acid may be cross-linked using a process such as divinyl sulfone or similar cross-linking technology. In some forms the hyaluronic acid may be esterified.

In some forms, the formulation includes a marker such as a visual or fluorescent marker. Example markers could include biocompatible excipients or food dyes such as brilliant blue (FD&C Blue #1), indigo carmine or similar, antioxidants such as ascorbic acid, fluorescent markers such as Fluorescein, indocyanine green (ICG), protoporphyrin IX or other surgical dyes such as patent blue V, trypan blue, isosulfan blue or methylene blue. The use of a marker gives a surgeon a visual cue to indicate the presence of the formulation on a nerve. This may aid the user in applying the formulation under-vision and to prevent repeated dosing over the same site. In some forms this enables the future identification of the labelled nerve and/or allows intra-axonal transport to delineate target organs or cell bodies for a particular nerve.

Also disclosed is use of a formulation as described during surgery. In some forms the use comprises applying the formulation to a nerve that has been exposed during surgery.

Disclosed is some forms is a composition comprising hyaluronic acid and dexamethasone. The composition in some forms is for use in the treatment and protection of nerves during surgery.

In some forms the hyaluronic acid is in the concentration of between 1% and 3% w/w. In some forms the concentration of hyaluronic acid is between approximately 10 mg/mL and 50 mg/mL, in some forms the concentration is 30 mg/mL.

In some forms the hyaluronic acid is in the form of sodium hyaluronate with a Molecular weight of 0.9 MDa (0.8-1.0) or a molecular weight of 2.1 MDa (2.0-2.3 MDa) But may be within the range 7 to 2300 kDa.

In some forms the formulation comprises hyaluronic acid with a substantially consistent molecular weight of approximately 0.9 MDa or a substantially consistent molecular weight of approximately between 0.8 and 1.0 MDa. In this form the formulation may have a concentration of approximately 5% w/w. In this form the formulation may include dexamethasone at a concentration of approximately 1 mg/mL.

In some forms the formulation comprises hyaluronic acid with a substantially consistent molecular weight of approximately 2.1 MDa or a substantially consistent molecular weight of approximately between 2.0 and 3.0 MDa. In this form the formulation may have a concentration of approximately 3% w/w. In this form the formulation may also include dexamethasone at a concentration of approximately 1 mg/mL.

In some forms the carrier may be an oligosaccharide of sodium hyaluronate. In some forms the carrier may be a sodium hyaluronate nanofiber or microfiber.

In some forms, the carrier has a consistent molecular weight and a consistent concentration. A consistent molecular weight in combination with a consistent concentration results in a reproducible viscosity and rheology.

In some forms the dexamethasone is in the form of dexamethasone phosphate. In some forms the dexamethasone phosphate is in the concentration of between 0.1 mg/mL and 10.0 mg/mL. In some forms the dexamethasone phosphate is in the concentration of approximately 1 mg/mL. In some forms the dexamethasone phosphate is in a concentration of 4 mg/mL.

In some forms the hyaluronic acid has a weight percentage between 0.5% and 5% w/w. In some forms the weight percentage of hyaluronic acid in the formulation is between 1% and 3%. In some forms the weight percentage of hyaluronic acid in the formulation is approximately 2%.

In some forms the dexamethasone is in the form of dexamethasone sodium phosphate. In some forms the dexamethasone sodium phosphate is in the concentration of between 0.5 mg/mL and 4.0 mg/mL. In some forms the dexamethasone sodium phosphate is in the concentration of approximately 1 mg/mL.

In some forms the composition further comprises one or more of creatinine, sodium citrate, sodium disulfite, methyl paraben, propyl paraben.

Further disclosed is use of a composition comprising hyaluronic acid and dexamethasone in the manufacture of a medicament for treatment and protection of nerves during surgery.

Disclosed is a method of treatment of an exposed nerve comprising delivering a composition comprising:

a matrix having one or more of a slow release effect and a viscosity that encourages maintenance of the location of the composition in the delivery location and a pharmacological active having one or more of a neuroprotective effect and a reduction of nerve dysfunction;

to an exposed nerve.

In some forms the matrix comprises a partially cross-linked hyaluronan hydrogel. In some forms the matrix has a pH=6.9-7.5. In some forms the hyaluronic acid has a concentration of approximately 1.5-2.0% w/w.

In some forms the rheology of the matrix limits the flow of the active away from a site of delivery. In some forms this allows for extended therapeutic effects. In some forms the elastic modulus of the matrix is between 100-200 Pa.

In some forms the carrier or matrix is adapted to slow release, to prolong the pharmacokinetics of the active pharmaceutical, and to reduce dissemination of the active pharmaceutical ingredient beyond the site at which its effect is intended. This may provide greater concentration of the active pharmaceutical to the relevant cells and limits waste.

In some forms the method comprises using a delivery device to deliver the composition.

In some forms the method is used in conjunction with a nerve monitor to enhance the process of locating a particular nerve and allow accurate deposit of the therapeutic formulation to the nerve. This provides a complete nerve solution by utilising both a diagnostic tool and a therapeutic formulation to treat and protect a nerve. Nerve monitors enable surgeons to identify, confirm, and monitor motor nerve function to help reduce the risk of nerve damage during various procedures.

Disclosed in some forms is a process for delivering a therapeutic substance during surgery. The method comprises loading a solid phase biodegradable scaffold with a therapeutic substance; positioning the scaffold during surgery such that the therapeutic substance is delivered to a desired location.

In some forms the therapeutic substance is selected from substances that can intervene in the activation of pathways of cellular degradation within the nerve.

In some forms the desired location is proximal or adjacent to a nerve. In some forms the therapeutic substance may be brought in contact with the nerve and/or allowed to coat the nerve.

In some forms the step of positioning the scaffold is performed upon exposure of the nerve during surgery.

In some forms the therapeutic substance is dexamethasone.

In some forms the therapeutic substance comprises a formulation comprising a biodegradable carrier and a therapeutic ingredient advantageous during tonsillectomy or sinus surgery.

In some forms the therapeutic ingredient comprises a local anaesthetic.

In some forms the therapeutic ingredient comprises an anti-inflammatory agent.

In some forms the therapeutic ingredient comprises an antibiotic.

In some forms the therapeutic ingredient comprises a haemostatic agent.

In some forms the therapeutic substance comprises a formulation comprising a biodegradable carrier and a therapeutic ingredient advantageous in treatment of burns or skin loss.

In some forms the therapeutic substance comprises a formulation comprising a biodegradable carrier and a chemotherapy agent.

Positioning of a chemotherapy agent during surgery allows for work around vital structures. For example when a cancer is located around a significant nerve the surgeon will wish to avoid damaging the nerve. The method allows for a long acting chemotherapy agent to be left on a tumour or evidence of residual disease for long term treatment.

Further, disclosed is a system comprising a solid phase biodegradeable scaffold with a therapeutic substance loaded thereon.

In some forms the scaffold further is further loaded with a haemostatic agent.

In some forms the therapeutic substance is selected from substances that can intervene in the activation of pathways of cellular degradation within the nerve.

In some forms the therapeutic substance is dexamethasone.

In some forms the carrier on which the therapeutic ingredient is loaded onto the scaffold is adapted to allow for ease of application of the therapeutic substance and associated pharmacological ingredient to a designated site during surgery and for concentration and efficiency. The carrier is, in some forms, adapted to reduce dissemination of the active pharmacological ingredient beyond the site at which its effect is intended. In some forms the carrier is adapted to localise the active pharmacological ingredient to the site at which its effect is intended.

The process allows controlled application of a therapeutic substance directly to a location such as a nerve, a burn site, a surgical site or a cancer. The application can limit or prevent peripheral damage, trauma or injury occurring during surgery and limit flow of the therapeutic substance beyond the intended site.

In some forms the step of applying the scaffold loaded with the therapeutic substance to the nerve is performed upon exposure of the nerve during surgery.

In some forms, the step of applying a therapeutic substance to the nerve is performed using a delivery device comprising a reservoir and an outlet, the therapeutic substance being delivered through the outlet.

In some forms actuation of the delivery device effects delivery of the formulation during the time at which the actuator is actuated.

The carrier in some forms is adapted to slow release, to prolong the pharmacokinetics of the active pharmaceutical, and to reduce dissemination of the active pharmaceutical ingredient beyond the site at which its effect is intended. This may provide greater concentration of the active pharmaceutical to the relevant cells and limits waste.

The carrier, in some forms, comprises natural polymers for example copolymers such as poly(lactic-co-glycolic acid), alginate, proteins, collagens, gelatin, fibrins, hyaluronan, polysaccharides, and albumin, or other synthetic polymers.

In some forms, the formulation includes a marker such as a visual or fluorescent marker. The use of a marker gives a surgeon a visual cue to indicate the presence of the formulation on a site. In some forms this enables the future identification of the labelled site and/or allows delineation of target sites.

The process and system are specifically described in relation to delivery of a formulation that can intervene in pathways of cellular degradation of a nerve or be used in treatment during tonsillectomy or sinus surgery, in treatment of burns or skin loss or in treatment of cancer through a chemotherapy agent during surgery. However it will be clear that the process of delivery can be utilised beyond the described circumstances.

Biocompatible materials used for fabrication of scaffolds for the purposes of delivery of a therapeutic substance may comprise natural polymers for example copolymers such as poly(lactic-co-glycolic acid), alginate, proteins, collagens, gelatin, fibrins, and albumin, or other synthetic polymers. In some forms the polymer comprises re-oxidised cellulose. In other forms bioceramics such as hydroxyapatites and tricalcium phosphates are used.

The structures are porous to allow delivery of drugs and genetic materials at a controlled rate over a period of time.

In some forms antibiotics or anti-inflammatory agents may be loaded onto the scaffold to prevent infection or inflammation after surgery.

In some forms the therapeutic substance is loaded through a biodegradable carrier such as hyalauronic acid for gradual sustained release.

Disclosed in some forms is a formulation comprising an active pharmacological ingredient having a neuroprotective effect and a carrier adapted to reduce dissemination of the active pharmacological ingredient beyond the site at which its effect is intended.

In some forms the active pharmacological ingredient is a corticosteroid.

In some forms the carrier is a depot matrix.

EXAMPLES

The following formulations are exemplary only and other formulations with alternative carriers, alternative active pharmaceuticals, alternative excipients and alternative concentrations will fall inside the scope of the claims and the scope of the disclosure.

Example 1

In the first example the formulation comprises hyaluronic acid in the form of Hyasis® 850 (10.0 mg/mL), dexamethasone sodium phosphate (4.0 mg/mL), creatinine, sodium citrate, sodium disulfite, methyl paraben, propyl paraben (pH 6.8)

The formulation was stored at 5, 25, and 37° C. for 210 days and the Hyaluronic Acid molecular weight was measured by SECMALS Results No significant polymer degradation was observed up to 210 days at 5 and 25° C.

Significant degradation was observed after 18 days at 37° C. most likely due to one or several excipients and/or their degradation products and the degradation products of dexamethasone (according to control experiments)

FIG. 1 shows the results in graphical form.

Example 2

Formulation: hyaluronic acid (10.0 mg/mL), dexamethasone sodium phosphate (4.0 mg/mL) (pH 6.8)

The formulation was stored at 5, 25, and 37° C. for 210 days and the Hyaluronic Acid molecular weight was measured by SECMALS Results No hyaluronic acid degradation was observed up to 210 days at 5 and 25° C. Dexamethasone and/or its degradation products most likely resulted in significant hyaluronic acid degradation after 30 days at 37° C.

Figure 2:
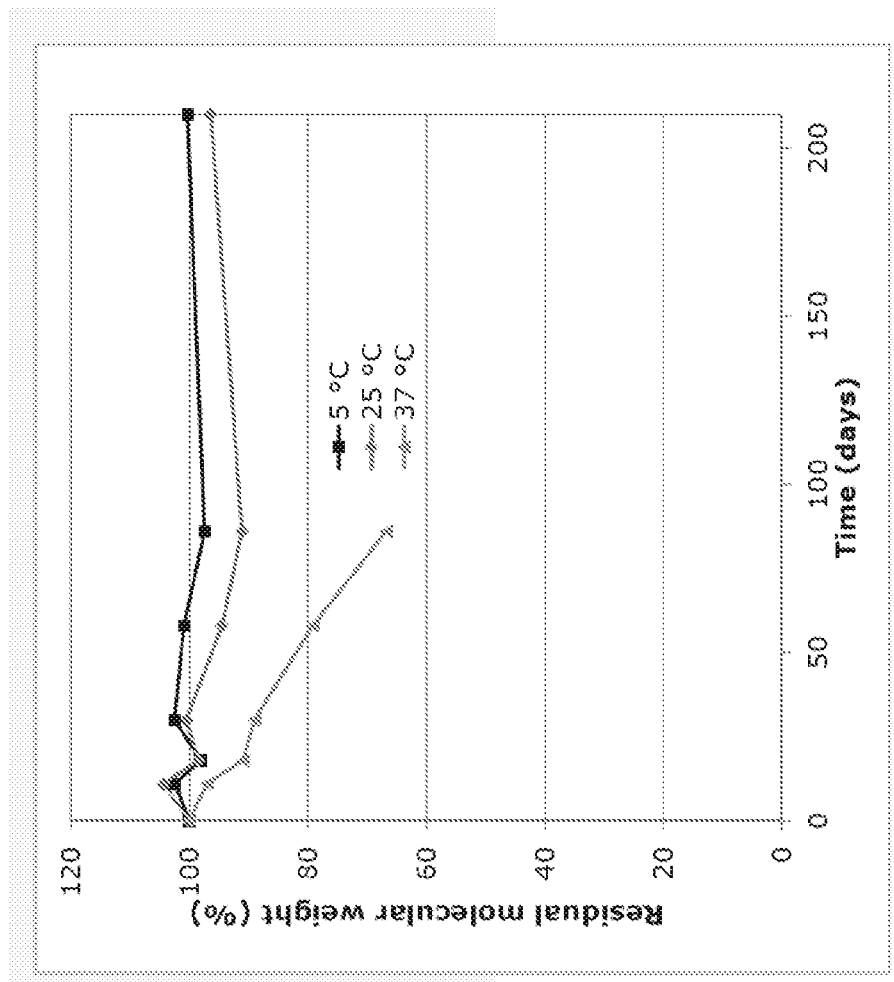
FIG. 2 is a graphical representation of molecular weight v time for hyaluronic acid with dexamethasone as in some embodiments of the disclosure.

FIG. 2 shows the results in graphical form.

Example 3

Formulation

Dexamethasone sodium phosphate (4.0 mg/mL), creatinine, sodium citrate, sodium disulfite, methyl paraben, propyl paraben (pH 6.8)

The formulation was stored at 5, 25, and 37° C. for 91 days and drug stability was assessed by HPLC Results:

No drug degradation was observed up to 91 days at 5 and 25° C. Heat and/or one or several excipients and/or their degradation products most likely resulted in significant API degradation after 28 days at 37° C.

Figure 3:
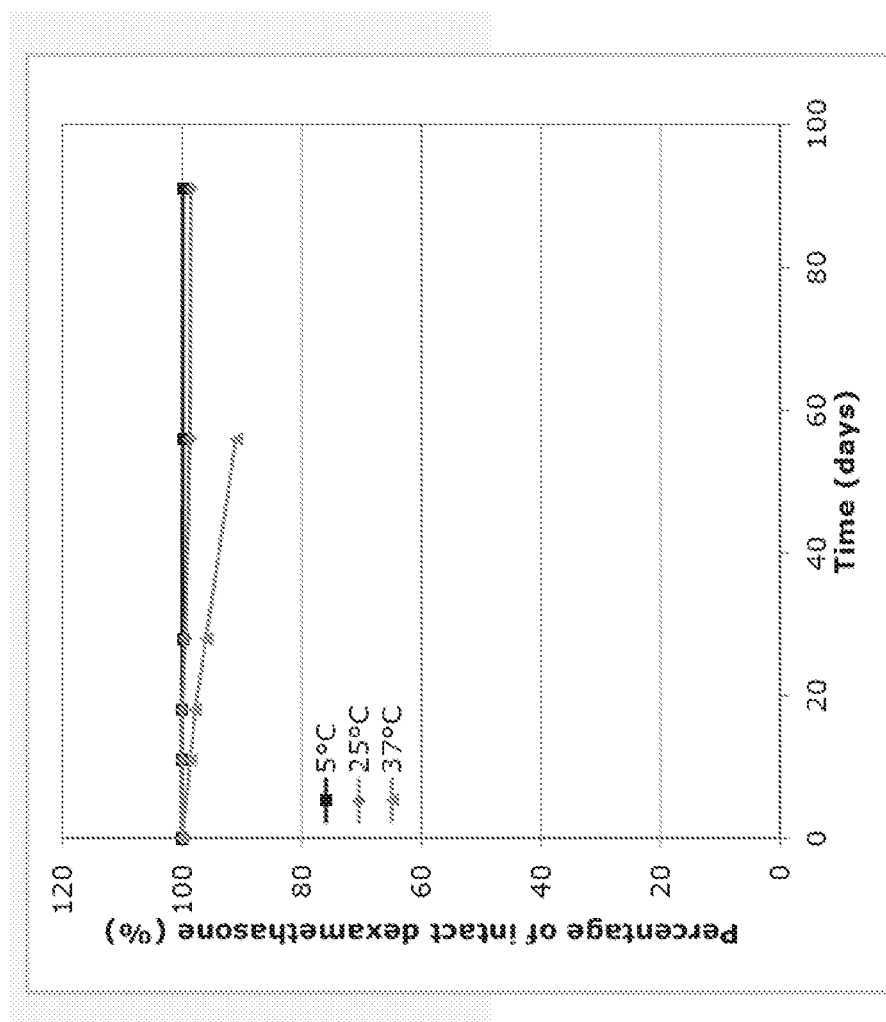
FIG. 3 graphical representation of drug stability v time for dexamethasone in the presence of excipients as in some embodiments of the disclosure.

FIG. 3 shows the results in graphical form.

Example 4

Formulation: hyaluronic acid (10.0 mg/mL), dexamethasone sodium phosphate (4.0 mg/mL) (pH 6.8)

The formulation was stored at 5, 25, and 37° C. for 91 days and drug stability was assessed by HPLC Results:

No drug degradation was observed up to 91 days at all Temperatures.

Figure 4:
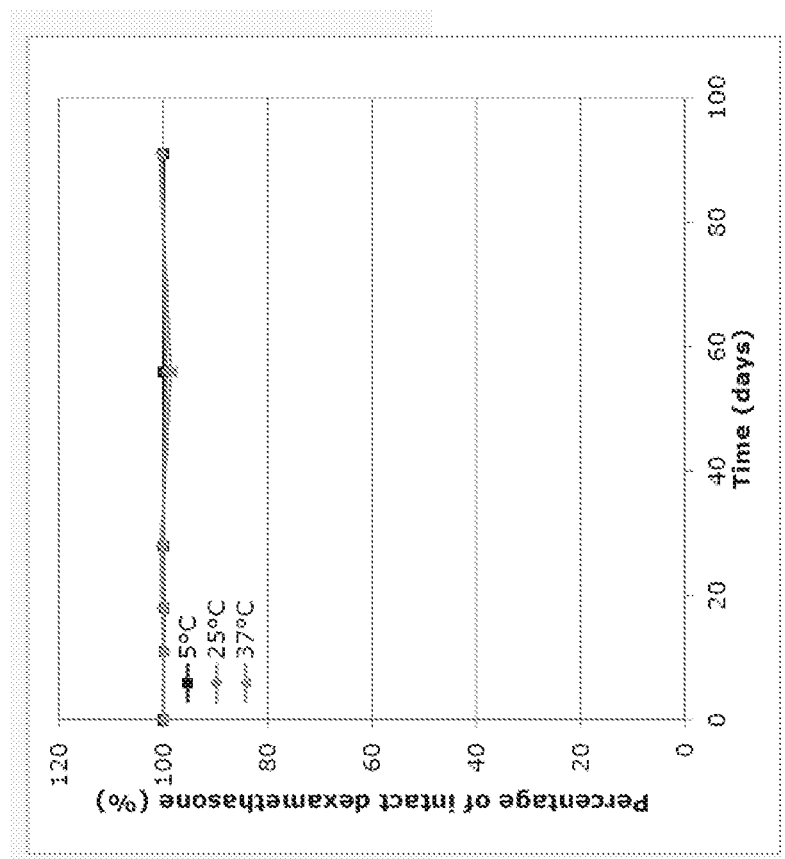
FIG. 4 is a graphical representation of drug stability v time for dexamethasone with hyaluronic acid as in some embodiments of the disclosure.

FIG. 4 shows the results in graphical form.

Example 5

Sodium Hyaluronate 3%+Dexamethosone 1 mg/ml+Brilliant Blue FCF (FD&C Blue #1).

Example 6

Sodium Hyaluronate 5%+Dexamethasone 2 mg/ml+Isosulfan Blue.

Example 7

Sodium Hyaluronate 5%+Dexamethasone 2 mg/ml+Fluroscien

Example 8

Sodium hyaluronate 3%+Dexamethasone 1 mg/ml+polyglycolic acid polymer (dyed)

Example 9

Sodium Hyaluronate 2%+Nicotinomide Mononucleotide (NMN)

Example 10

Sodium Hyaluronate 3%+Dexamethasone+Nicotinomide Mononucleotide (NMN)

Example 11

Sodium Hyaluronate 2%+Nicotinomide riboside

It is to be understood that, if any prior art publication is referred to herein, such reference does not constitute an admission that the publication forms a part of the common general knowledge in the art, in Australia or any other country.

In the claims which follow and in the preceding description of the disclosure, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

What is claimed is:

1. A method for protection of one or more nerves during surgery, the method comprising the successive steps of:
   A) performing surgery including making an incision, a length of a nerve being exposed by the incision, the length of the nerve being able to be identified visually;
   B) visually identifying the length of the exposed nerve;
   C) applying a formulation directly along the length of the exposed nerve, the formulation comprising an active pharmacological ingredient adapted to intervene in the activation of pathways of cellular degradation within the one or more nerves, and a carrier adapted to localise application of the formulation to the exposed length of the nerve and reduce dissemination of the active pharmacological ingredient beyond the exposed length of the nerve; and
   D) closing the incision made in step A).

2. A method as defined in claim 1, wherein the formulation is in a flowable form and comprises an active pharmacological ingredient and a carrier.

3. A method as defined in claim 2 wherein the carrier is a depot matrix.

4. A method as defined in claim 2, wherein the carrier is adapted to slow the release of the active pharmacological ingredient.

5. A process of protecting a nerve during surgery, the process comprising the successive steps of:
   A) performing surgery including making an incision, a length of nerve being exposed by the incision, the length of nerve exposed being able to be visually identified,
   B) identifying the exposed nerve,
   C) applying a formulation directly along the exposed length of the nerve, the formulation comprising an active pharmacological ingredient adapted to intervene in the activation of pathways of cellular degradation within the nerve, and a carrier adapted to localise application of the formulation to the exposed nerve and reduce dissemination of the active pharmacological ingredient beyond the nerve, and
   D) closing the incision made in step A).

6. A process as defined in claim 5, further comprising the step of monitoring the nerve function by monitoring EMG activity from muscles innervated by the exposed nerve.

7. A process as defined in claim 5, wherein the step of identifying a nerve is performed using a nerve monitor.

8. A process as defined in claim 5, wherein the formulation is in a flowable form when applied to the nerve.

* * * * *